(12) United States Patent
Rigby

(10) Patent No.: US 8,278,107 B2
(45) Date of Patent: Oct. 2, 2012

(54) COMPOSITIONS AND METHODS FOR REGULATING RNA TRANSLATION VIA CD154 CA-DINUCLEOTIDE REPEAT

(75) Inventor: William F. C. Rigby, Etna, NH (US)

(73) Assignee: Trustees of Dartmouth College, Hanover, NH (US)

( * ) Notice: Subject to any disclaimer, the term of this patent is extended or adjusted under 35 U.S.C. 154(b) by 75 days.

(21) Appl. No.: 12/699,180

(22) Filed: Feb. 3, 2010

(65) Prior Publication Data

US 2010/0136568 A1 Jun. 3, 2010

Related U.S. Application Data

(63) Continuation-in-part of application No. PCT/US2008/075965, filed on Sep. 11, 2008, which is a continuation-in-part of application No. PCT/US2006/035260, filed on Sep. 11, 2006, application No. 12/699,180, which is a continuation-in-part of application No. 12/064,471, filed on Feb. 22, 2008, and a continuation-in-part of application No. 11/854,148, filed on Sep. 12, 2007.

(60) Provisional application No. 60/716,708, filed on Sep. 13, 2005.

(51) Int. Cl.
*C12N 15/85* (2006.01)
*C07H 21/04* (2006.01)

(52) U.S. Cl. .................... 435/455; 435/325; 536/24.5

(58) Field of Classification Search ................ None
See application file for complete search history.

(56) References Cited

U.S. PATENT DOCUMENTS

| | | | |
|---|---|---|---|
| 7,022,487 B2 | 4/2006 | Rigby | 435/7.1 |
| 7,345,027 B2 | 3/2008 | Tolentino et al. | 514/44 |
| 2005/0096282 A1 | 5/2005 | Lewin et al. | 514/44 A |

OTHER PUBLICATIONS

Anwar et al., "Demonstration of Functional Requirement of Polypyrimidine Tract-Binding Protein by SELEX RNA during Hepatitis C Virus Internal Ribosome Entry Site-Mediated Translation Initiation" The Journal of Biological Chemistry 2000 275 (44):34231-34235.
Citores et al., "The Dinucleotide Repeat Polymorphism in the 3' UTR of the CD154 Gene has a Functional Role on Protein Expression and is Associated with Systemic Lupus Erythematosus" 2004 Ann. Rheum. Dis. 63:310-317.
Hamilton et al., "Delineation of a Novel Pathway that Regulates CD154 (CD40 Ligand) Expression" 2003 Molecular and Cellular Biology 23(2):510-125.
Hui et al, "Novel Functional Role of CA Repeats and hnRNP L in RNA Stability" 2003 RNA 9:931-936.
Kosinski et al., "A Complex Containing Polypyrimidine Tract-Binding Protein is Involved in Regulating the Stability of CD40 Ligand (CD154) mRNA" 2003 The Journal of Immunology 170 (2):979-988.
Singh et al., "Distinct Binding Specificities and Functions of Higher Eukaryotic Polypyrimidine Tract-Binding Proteins" 1995 Science 268:1173-1176.
Jenks, B. G. "Regulation of *Proopiomelanocortin* Gene Expression An Overview of the Signaling Cascades, Transcription Factors, and Responsive Elements Involved" 2009 Annals of the New York Academy of Sciences 1163:17-30.
NCBI Genbank Association No. NP_001005335 [gi:52632385] with Revision History—Sep. 24, 2004-Oct. 18, 2005.
NCBI Genbank Association No. NP_001524 [gi:52632383] with Revision History—Apr. 1, 1999-Oct. 18, 2005.
Office Communication dated Jul. 13, 2009 from U.S. Appl. No. 12/064,471, filed Feb. 22, 2008.
Office Communication dated Sep. 18, 2009 from U.S. Appl. No. 12/064,471, filed Feb. 22, 2008.
Office Communication dated Feb. 24, 2010 from U.S. Appl. No. 12/064,471, filed Feb. 22, 2008.
Office Communication dated Jul. 29, 2009 from U.S. Appl. No. 11/854,148, filed Sep. 12, 2007.
Office Communication dated Oct. 27, 2009 from U.S. Appl. No. 11/854,148, filed Sep. 12, 2007.
Office Communication dated Mar. 12, 2010 from U.S. Appl. No. 11/854,148, filed Sep. 12, 2007.

*Primary Examiner* — Celine Qian
(74) *Attorney, Agent, or Firm* — Licata & Tyrrell P.C.

(57) ABSTRACT

Compositions and methods for regulating CD154 gene expression are provided that rely on the interaction of hnRNP L with the CA-dinucleotide rich sequence of the 3'-untranslated region of CD154.

1 Claim, No Drawings

COMPOSITIONS AND METHODS FOR REGULATING RNA TRANSLATION VIA CD154 CA-DINUCLEOTIDE REPEAT

This application is a continuation-in-part application of PCT/US2008/075965 filed Sep. 11, 2008, which is a continuation-in-part application of PCT/US2006/035260, filed Sep. 11, 2006, which claims benefit of U.S. Provisional Patent Application Ser. No. 60/716,708, filed Sep. 13, 2005. This application is also a continuation-in-part of Ser. No. 12/064,471 filed Feb. 22, 2008 and a continuation-in-part of Ser. No. 11/854,148 filed Sep. 12, 2007, which both also claim benefit of U.S. Provisional Patent Application Ser. No. 60/716,708, filed Sep. 13, 2005, the contents of which are incorporated herein by reference in their entireties.

This invention was made in the course of research sponsored by the National Institutes of Health (NIH Grant No. AI34928). The U.S. government has certain rights in this invention.

BACKGROUND OF THE INVENTION

The expression of CD154 (CD40 ligand), a member of the Tumor Necrosis Factor (TNF) gene family, by activated T lymphocytes is critical in the development of humoral and cell-mediated immunity (Foy, et al. (1996) Annu. Rev. Immunol. 14:591-617; Grewal & Flavell (1998) Ann. Rev. Immunol. 16:111-135; Hollenbaugh, et al. (1994) Immunol. Rev. 138:23-37; Noelle (1996) Immunity 4:415-419). CD154 blockade retards the development and progression of immune responses in an array of transplantation and autoimmune disease models ranging from Systemic Lupus Erythematosus to Rheumatoid Arthritis to Multiple Sclerosis (Foy, et al. (1996) supra; Grewal & Flavell (1998) supra). Resting T cells express little or no CD154 (Lane, et al. (1992) Eur. J. Immunol. 22:2573-2578; Nusslein, et al. (1996) Eur. J. Immunol. 26:846-850; Roy, et al. (1993) J. Immunol. 151:2497-2510) and signals (anti-CD3, mitogenic lectins) that trigger resting T cells to engage in high levels of proliferation and cytokine production, elicit little (CD4+ T cells) or no (CD8+ T cells) expression on either mouse or human T cells (Lane, et al. (1992) supra; Nusslein, et al. (1996) supra; Roy, et al. (1993) supra), suggesting different pathways of gene regulation. Maximal expression of CD154 requires pharmacologic stimulation provided by phorbol myristate acetate (PMA) and calcium ionophores such as ionomycin (Lane, et al. (1992) supra; Nusslein, et al. (1996) supra; Roy, et al. (1993) supra; Roy, et al. (1994) Eur. J. Immunol. 25:596-603). Cyclosporine and glucocorticoids block CD154 induction on T lymphocytes; these effects are presumed to be transcriptional (Fuleihan, et al. (1994) J. Clin. Invest. 93:1315-1320; Roy, et al. (1993) supra), based on the presence of NF-AT sites in the CD154 promoter (Schubert, et al. (1995) J. Biol. Chem. 15:29264-29627). Since cyclosporine and glucocorticoids also inhibit cytokine production (Ashwell, et al. (1992) Ann. Rev. Immunol. 18:309-345; Sigal & Dumont (1992) Ann. Rev. Immunol. 10:519-60), this pathway does not account for the differential regulation of CD154 expression by T lymphocytes.

CD154 mRNA has been shown to be unstable in activated T lymphocytes, with a half-life (~30 minutes) approximating that seen with interleukins-2 (IL-2; Ford, et al. (1999) J. Immunol. 162:4037-4044; Murakami, et al. (1999) J. Immunol. 163:2667-2673; Rigby, et al. (1999) J. Immunol. 163:4199-4206; Suarez, et al. (1997) Eur. J. Immunol. 27:2822-2829). Nevertheless, several studies indicate that cytokine (IL-2 and TNF-alpha) and CD154 mRNA stability and expression are regulated through distinct pathways (Ford, et al. (1999) supra; Lindsten, et al. (1989) Science 244:339-343; Murakami, et al. (1999) supra). A region (nucleotides 468-835 referenced to the translational stop site) within the 986 nucleotide human CD154 3'-untranslated region (3'-UTR) confers an increase in the rate of mRNA turnover to chimeric reporter gene constructs in vivo (Hamilton, et al. (2003) Mol. Cell. Biol.; 23(2):510-25). This region lacks canonical AURE-type sequences, containing a polypyrimidine rich element as well as CA-dinucleotide repeat and polycytidine sequences. Members of the human polypyrimidine tract binding protein (PTB) gene family were identified and shown to directly interact with cytidines and uridines within this region (Hamilton, et al. (2003) supra; kosinski, et al. (2003) J. Immunol. 170(2):979-88), consistent with the presence of multiple PTB consensus binding sites (Anwar, et al. (2000) J. Biol. Chem. 275:34231-34235; Singh, et al. (1995) Science 268:1173-1176). Overexpression of splice isoforms of the PTB proteins differentially regulates CD154 expression and mRNA accumulation in a 3'-UTR-dependent manner in cell lines and normal human T cells. These effects are specific and restricted to reporter constructs containing the 3'-UTR polypyrimidine rich region.

The murine CD154 (mCD154) 3'-UTR is ~0.3 kb shorter than its human counterpart, due to a 292 nucleotide insertion present at the 5' end of the human 3'-UTR. The remaining portion of the human and entire mCD154 3'-UTR exhibits 70% conservation with retention of the polycytidine, polypyrimidine, and CA-dinucleotide repeat regions as well as an AURE that is found immediately 5' of the polyadenylation signal sequence. Murine CD154 3'-UTR inhibits luciferase mRNA accumulation and protein activity in a comparable manner relative to that seen with the human CD154 3'-UTR. Further, deletion of the polypyrimidine-rich region cis-acting element enhances inhibition of 3'-UTR-dependent gene expression.

A novel pathway has now been identified which regulates translation of CD154 mRNA.

SUMMARY OF THE INVENTION

The present invention embraces methods for modulating the translation of a ribonucleic acid that contains CA-dinucleotide rich sequences. Identification of this sequence and its function due to hnRNP L interactions raises the possibility that small molecule inhibitors can be identified that can regulate its activity in the context of the CD154 3'-UTR or any other gene that contains a similar sequence. The methods involve contacting a cell or tissue containing a CA-dinucleotide rich sequence of the CD154 mRNA 3'-untranslated region operatively-linked to a ribonucleic acid with an agent that binds to the CA-dinucleotide rich sequence of the CD154 mRNA 3'-untranslated region or an agent which modulates the level or activity of an hnRNP L protein so that the nuclear export or translation of the ribonucleic acid is modulated.

The present invention also encompasses methods for preventing or treating a disease or condition associated with CD154-CD40 interactions. These methods involve administering to a subject in need of treatment an agent which binds to a CA-dinucleotide rich sequence of the CD154 mRNA 3'-untranslated region or an agent which modulates the level or activity of hnRNP L protein so that CD154 translation is inhibited thereby preventing or treating the disease or condition associated with CD154-CD40 interactions.

The present invention further provides a method for identifying agents that modulate the level or activity of hnRNP L. This method of the invention involves contacting a test cell containing hnRNP L protein, and a CA-dinucleotide rich sequence of the CD154 mRNA 3'-untranslated region operatively-linked to a nucleic acid encoding a reporter protein, with an agent and detecting reporter protein expression in the test cell. A decrease in reporter protein expression in the test cell contacted with the agent relative to reporter protein expression in a test cell not contacted with the agent, indicates that the agent increases the level or activity of hnRNP L in the cell. An increase in reporter protein expression in the test cell contacted with the agent relative to reporter protein expression in a test cell not contacted with the agent, indicates that the agent decreases the level or activity of hnRNP L in the cell.

These and other aspects of the present invention are set forth in more detail in the following description of the invention.

DETAILED DESCRIPTION OF THE INVENTION

The human and murine CD154 3'-UTR are highly conserved, except for the presence of a 293 nucleotide insertion immediately after the translational stop site. Most notable are the presence of adjacent CU- and CA-rich regions. In addition, the murine CD154 3'-UTR contains polycytidine and AU-rich element sequences that are expanded relative to its human counterpart. The CA-rich region is of interest as it represents an extended series of CA-dinucleotide repeats, which are almost always intronic. Chimeric reporter gene constructs have indicated that a cis-acting element of the human CD154 3'-UTR maps to a region containing both the CU- and CA-rich domains. This effect was present in multiple cell lines (Jurkat, HeLa) as well as normal human T cells.

To delineate the mCD154 3'-UTR sequences involved in regulating CD154 expression, chimeric luciferase reporter gene constructs were generated and transiently transfected into HeLa cells. The presence of the mCD154 3'-UTR markedly reduced luciferase expression. Prior studies with the human CD154 3'-UTR indicate that cytoplasmic levels of PTB proteins regulate the function of this element. The binding specificity of PTB proteins, among other factors, indicate that the CU-rich domain (also referred to herein as CURE) is the major cis-acting element in the human CD154 3'-UTR. However, deletion of the CURE from mCD154 3'-UTR resulted in a decrease rather than an increase in luciferase activity. Deletion of the CA-rich domain (also referred to herein as CARE) provided a similar effect. Accordingly, both the CURE and CARE domains in the CD154 3'-UTR function as cis-acting elements.

To eliminate the possibility that deletion of either the CURE or CARE domains enhances the function of a secondary cis-acting element, both the CURE and CARE domains were deleted. This mutation increased luciferase activity to 171% of that seen with control. Superimposing mutation of the polycytidine (poly C) or ARE sequences in the context of deleting the CURE and CARE elements in the CD154 3'-UTR had no additional effect on luciferase expression. These data indicate that the CURE and CARE regions each function as cis-acting elements to regulate expression of CD154. An identical pattern was observed with transient transfection of human peripheral blood mononuclear cells (PBMC) under basal and activated conditions. Insertion of the CURE (CARE+) or CARE (CARE+) alone in the 3'UTR of reporter genes established that each cis-acting element was sufficient to reduce luciferase activity and poly(A)+ mRNA levels. Thus, the effects of both the CURE and the CARE alone are transferable in the 3'UTR of heterologous transcripts.

Following transient transfection of HeLa cells, RNA was extracted and luciferase mRNA levels quantified by real-time RT-PCR. Deletion of either the CURE or the CARE region had no significant effect on steady-state mRNA levels. Deletion of both CURE and CARE regions increased luciferase mRNA expression. These data indicated that both the CURE and CARE regions regulated CD154 mRNA turnover. Using a HeLa Tet-Off™ system, identical constructs were generated containing either the CURE or CARE region. HeLa cells were transiently transfected overnight and transcription was inhibited by the addition of doxycycline. Cytoplasmic RNA was collected at time 0 and at various times thereafter. Luciferase mRNA levels measured by real-time RT-PCR indicated that at time 0, steady state levels of cytoplasmic luciferase mRNA were reduced by the presence of CD154 3'-UTR containing either the CURE or CARE regions. The presence of the mCD154 3'-UTR increased luciferase mRNA turnover relative to controls, as seen with the human 3'-UTR. Deletion of both CURE and CARE regions increased luciferase mRNA stability to that of controls. Similarly, the CARE-deletion (CARE−) still exhibited an increased rate of decay, indicating a role of the retained CURE in mRNA decay. Surprisingly, deletion of the CURE (CURE−) element increased the stability of cytoplasmic poly (A)+ mRNA to that of the control vector, although it inhibited luciferase expression and poly(A)+ mRNA accumulation. These data indicated that the retained CARE functioned independently of mRNA decay to limit steady state levels of luciferase poly(A) RNA.

To determine how the CARE region reduces cytoplasmic mRNA levels in the absence of effects on mRNA stability, the contribution of other portions of the mCD154 3'-UTR were eliminated. Isolated CURE and/or CARE regions were cloned into the 3'-UTR of the pTRE vector and luciferase activity and mRNA turnover examined. This analysis indicated that the CURE alone (CURE+) conferred increased mRNA decay, establishing that it alone promotes cytoplasmic mRNA instability. When combined with the observed stability of the CURE− reporter, these data indicate that the instability associated with the CD154 3'-UTR derives from the CURE. In contrast, the CARE element alone (CARE+) had no effect on the decay of poly(A)+ mRNA, despite reducing luciferase RNA to an equivalent degree. Thus, both in isolation as well as in the context of the CD154 3'-UTR (CURE−), the CARE reduces luciferase activity and poly(A)+ mRNA levels independent of cytoplasmic decay.

The 3'-UTR CARE reduced poly (A)+ mRNA levels without increasing mRNA decay, prompting examination of its function as a transcriptional silencer when placed downstream of the reporter gene. No effect was seen. Since prior measurements of reporter mRNA by quantitative RT-PCR relied on the use of cytoplasmic poly(A)+ mRNA, it was determined whether these results were potentially influenced by an effect of the 3'-UTR CARE on mRNA polyadenylation. Total cytoplasmic RNA was analyzed by RT-PCR in which the effect of priming with either oligo d(T) or random hexamers was compared. The 3'-UTR CURE alone reduced luciferase mRNA levels independent of priming, consistent with its effects on cytoplasmic mRNA decay. In contrast, the 3'-UTR CARE alone increased by >3-fold the apparent levels of input luciferase RNA seen with random hexamer priming relative to that seen with oligo d(T). Similar results were seen in which luciferase-specific priming of reverse transcription was used instead of random hexamers.

Since oligo d(T)-, but not random hexamer-dependent priming was affected by the 3'-UTR CARE, it was determined whether luciferase mRNA polyadenyation was affected using Ligase-Mediated Polyadenylation Tail Assay (LM-PAT) of cytoplasmic RNA (Salles, et al. (1999) Methods. 17:38-45). The presence of the 3'-UTR CARE reduced the poly(A) tail to <50 adenylates, relative to the control and 3'-UTR CURE reporter mRNA where poly (A) tails as long as 150 bases were seen. The effect of the 3'-UTR CARE on poly(A) tail length was equally apparent in both nuclear and cytoplasmic extracts. These data indicate that the effect of the 3'-UTR CARE on poly(A) tail length is transduced in the nucleus. Finally, it was demonstrated that CD154 mRNA polyadenylation is regulated in normal murine T cells. Under resting and early (6 hours) activation conditions, nearly all CD154 mRNA was found to be deadenylated. At 24 hours, CD154 mRNA poly(A) tail length increased. Thus, CD154 mRNA polyadenylation is regulated as a function of activation. This was not a generalized effect on all mRNA, as examination of TNF mRNA exhibited a distinct pattern of modulation of poly(A) tail length.

Experiments were performed to characterize, purify and identify the protein(s) binding to and regulating expression of CD154 via the CARE sequence. Using activated human peripheral blood mononuclear cells, immunoprecipitation followed by RNA extraction and RT-PCR established that PTB and hnRNP L each bind native CD154 mRNA in vivo. GAPDH RNA was not found in these immunoprecipitates, establishing the specificity of this interaction. Moreover, immunoblotting demonstrated that PTB and hnRNP L coprecipitate. The specificity of the hnRNP L interaction with the murine CD154 3'-UTR and CARE in vivo was examined. Following transient transfection of HeLa cells with reporter vectors that lacked (control) or contained these sequences, hnRNP L immunoprecipitates were analyzed for the presence of luciferase mRNA. Luciferase mRNA was coprecipitated with hnRNP L in a 3'-UTR CARE-dependent manner. The specificity of this interaction of hnRNP L was shown both by the absence or GAPDH or a luciferase mRNA lacking a 3'-UTR CARE in the immunoprecipitates.

The functional significance of the hnRNP L-3'-UTR CARE interaction was tested. Knockdowns of hnRNP L levels by RNA interference eliminated the inhibitory effects of the 3'-UTR CARE on luciferase expression and poly (A) tail length. Overexpression of hnRNP L strikingly enhanced the activity of the 3'-UTR CARE, increasing the inhibition of luciferase activity from ~50% to 90%. This enhanced suppression was accompanied by increased luciferase mRNA deadenylation as measured by oligo d(T) priming or LM-PAT assays. These results indicated that hnRNP L binds the 3'-UTR CARE in vivo to regulate nuclear polyadenylation. Thus, when cytoplasmic levels of hnRNP L are low, CD154 mRNA is translated more efficiently and increased surface expression of CD154 results.

These data demonstrate the existence of a novel pathway of mRNA turnover regulation. Additionally, these data indicate that the polymorphic nature of CARE in CD154 3'-UTR may influence CD154 expression and immune responses. The presence of CARE could influence mRNA biogenesis both at the level of splicing and mRNA stability. Further, the relative levels of cytoplasmic hnRNP L appear to be regulated by specific stimuli and modulating the levels of hnRNP L could be used as a means of modulating the expression of CD154 at the level of translation and nuclear export. Accordingly, inhibiting CD154 expression at the level of hnRNP L expression or activity or the CARE is useful in autoimmune and inflammatory diseases, whereas enhancing expression of CD154 by targeting this pathway could be used in immunotherapy of cancer or for augmenting immune responses in immunodeficient individuals. In particular, it is contemplated that several potential pathways may lead to increased CD154 mRNA polyadenylation as a function of duration of T cell activation. These include a decline in nuclear levels of hnRNP L or its ability to interact with the CARE. Alternatively, the ability of hnRNP L molecules to homodimerize may be influenced by T cell activation, perhaps due to post-translational modification. Third, prolonged T cell activation is associated with increases in the levels of PTB proteins and increased levels of PTB might limit hnRNP L-hnRNP L homodimer formation. Each mechanism may limit recruitment of deadenylases or polyadenylation factors to the mRNA transcript.

Precise regulation of CD154 is critical in immunoregulation; transgenic overexpression of CD154 results in a phenotype suggestive of Systemic Lupus Erythematosus (SLE) (Clegg, et al. (1997) Int. Immunol. 9(8):1111-22; Dunn, et al. (1997) J. Histochem. Cytochem. 45(1):129-41; Mehling, et al. (2001) J. Exp. Med. 194(5):615-28; Higuchi, et al. (2002) J. Immunol. 168(1):9-12). T cells from patients with SLE exhibit enhanced surface expression of CD154, particularly after 24 hours (Koshy, et al. (1996) J. Clin. Invest. 98(3):826-37). The 3'-UTR CARE is polymorphic in humans and increased CA repeats (>24) have been reported to occur at increased frequency in patients with SLE (Citores, et al. (2004) Ann. Rheum. Dis. 63(3):310-7). Characterization of the function of this cis-acting element and its regulation by hnRNP L provides a novel means to treat this disease.

Moreover, soluble CD154 derived from platelets has been associated with both acute coronary syndromes as well as increased risk for cardiovascular disease. Thus, targeting hnRNP L or the CARE may be useful in treatment of acute and chronic atherosclerotic disease including angina, myocardial infarction, stroke and other conditions of acute or chronic vascular insufficiency.

Thus, the present invention embraces methods of modulating nuclear export or translation of a ribonucleic acid molecule operatively-linked to a CARE sequence of the CD154 mRNA 3'-untranslated region using an agent which binds to the CARE sequence or which modulates the level or activity of an hnRNP L protein so that the nuclear export or translation of the ribonucleic acid is modulated. Operatively-linked is intended to mean that the ribonucleic acid is linked to the CARE sequence in a manner which allows for translation of the ribonucleic acid molecule to be regulated by the CARE sequence, i.e., the ribonucleic acid molecule and CARE sequence are located on the same transcript.

As used herein, the CARE sequence of the CD154 mRNA 3'-untranslated region (3'-UTR) is located between nucleotides 468 to 835 of the human CD154 3'-UTR cDNA relative to the translational stop site; i.e., within the BstNI-HphI restriction enzyme fragment of the 3'-UTR. This region is set forth herein as SEQ ID NO:1:

Caggctctagaacgtctaacacagtgggagaaccgaaaccccccccccccccc ccgccaccctctcggacagttattcattctctttcaatctctctctctccatctctctc tttcagtctctctctctcaacctctttcttccaatctctctttctcaatctctctgttt ccctttgtcagtctcttccctcccccagtctctcttctctcccccctttctaacacacac acacacacacacacacacacacacaca- cacacacacacacacacacacacacacacaga gtcaggccgttgctagtcagt- tctcttctttccaccctgtccctatctctaccactata gatgagggtgaggagtag (SEQ ID NO:1), wherein the CARE repeat is underlined and located at positions 223 to 286 of SEQ ID NO:1.

Methods of modulating or regulating translation of an RNA molecule operatively-linked to a CARE sequence of a CD154 3'-UTR encompass both enhancing and inhibiting the translation of said RNA molecule. Binding of an agent, e.g., an siRNA or hnRNP L (GENBANK Accession No. NP_001005335 or NP_001524) to the CARE or increasing the expression or activity of hnRNP L via an agent results in inhibition of translation of the RNA molecule. Conversely, decreasing the expression or activity of hnRNP L via an agent (e.g., an siRNA) enhances translation of the RNA molecule. Effects on translation of the RNA can be determined using standard techniques such as western blot analysis of the translated product of the RNA sequence, or if the protein being translated is an enzyme, enzymatic assays can be performed. In particular embodiments, the ribonucleic acid molecule encodes CD154. As such, binding of an agent to the CARE or increasing the level or activity of hnRNP L by pharmacological agents is contemplated as a useful tool in the treatment of autoimmune and inflammatory diseases which are associated with CD154-CD40 interactions, whereas decreasing the level or activity of hnRNP L by pharmacological agents is contemplated as a useful tool in the treatment of, e.g., cancer, wherein CD40 activation by CD154 is advantageous.

Thus, the present invention also encompasses methods for preventing or treating a disease or condition associated with B cell CD154-CD40 interactions, i.e., diseases or conditions resulting from enhanced CD40 activation by CD154, or diseases or conditions associated with lack of CD40 activation by CD154. The methods involve administering to a subject in need of treatment an agent which binds to a CA-dinucleotide rich sequence of the CD154 mRNA 3'-untranslated region or an agent that increases the level or activity of hnRNP L protein so that CD154 translation is inhibited thereby preventing or treating the disease or condition associated with CD40 activation by CD154. Diseases or conditions which can be prevented or treated in accordance with the instant method, include, but are not limited to, allograft rejection; allergy (including anaphylaxis); atherosclerosis including angina, myocardial infarction, stroke and other conditions of chronic or acute vascular insufficiency; autoimmune conditions including drug-induced lupus, systemic lupus erythematosus, adult rheumatoid arthritis, juvenile rheumatoid arthritis, scleroderma, Sjogren's Syndrome, etc.; and viral diseases that involve B-cells, including Epstein-Barr infection, cancer, and retroviral infection including infection with a human immunodeficiency virus. Because it has been suggested that B cell activation is associated with the induction of human immunodeficiency virus replication from latency, it may be desirable to decrease translation of CD154 mRNA in HIV positive individuals who have not yet developed AIDS or ARC.

In particular embodiments, the subject is a primate, such as a human. In other embodiments, the subject is a mammal of commercial importance, or a companion animal or other animal of value. Thus, subjects also include, but are not limited to, sheep, horses, cattle, goats, pigs, dogs, cats, rabbits, guinea pigs, hamsters, rats and mice.

It is contemplated that the agent can be administered as a capsule, intramuscularly, intraperitoneally, subcutaneously, intradermally or applied locally to a wound site. It is also clear that the invention can be used with a skin graft procedure. The skin is a notoriously difficult tissue with which to achieve or maintain engraftment. A preferred route of administration for treating or preventing skin graft rejection is topical, subdermal, intradermal or subcutaneous, though systemic and other routes are also contemplated.

Another route of administration for skin graft includes direct application locally (by topical application, immersion or bath, or local injection) into the subject tissue bed, or to the graft tissue itself. High local concentrations of the agent, particularly in areas of lymphatic drainage, are expected to be particularly advantageous. Alternatively, the graft tissue can be transfected or transformed with a recombinant expression vector to overexpress hnRNP L.

An effective amount of an agent which binds to a CARE sequence of the CD154 mRNA 3'-untranslated region or an agent that alters the level or activity of hnRNP L protein is an amount which decreases or inhibits the signs or symptoms of diseases or conditions associated with CD40 activation (e.g., edema, fever, and loss of graft function) and will be dependent on the nature of the agent.

Agents useful in accordance with the methods provided herein include, but are not limited to, purified hnRNP L protein, a recombinant expression vector expressing hnRNP L, a recombinant expression vector expressing an siRNA which binds the CARE sequence or hnRNP L RNA, organic molecules, biomolecules including peptides, antibodies, saccharides, fatty acids, steroids, purines, pyrimidines, derivatives, structural analogs or combinations thereof.

An isolated or purified protein hnRNP L protein for administrating PTB or PTB-T protein administration to a cell or tissue can be produced by various means. An isolated or purified protein is substantially free of cellular material or other contaminating proteins from the cell or tissue source from which the hnRNP L protein is derived. To be substantially free of cellular material includes preparations of hnRNP L protein in which the protein is separated from cellular components of the cells from which it is isolated or recombinantly produced. When the hnRNP L protein is recombinantly produced, it is also preferably substantially free of culture medium.

Recombinant production of hnRNP L protein typically involves generating a fusion protein such as a GST-hnRNP L in which the hnRNP L protein sequence is fused to the C-terminus of the GST sequence. Such fusion proteins can facilitate the purification of recombinant hnRNP L protein. Alternatively, the fusion protein is a hnRNP L protein containing a heterologous signal sequence at its N-terminus. In certain host cells (e.g., mammalian host cells), expression and/or secretion of hnRNP L protein can be increased through use of a heterologous signal sequence. Preferably, a hnRNP L chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. Alternatively, the fusion gene can be synthesized by conventional techniques including automated DNA synthesizers or PCR amplification. PCR amplification of gene fragments can be carried out using anchor primers which give rise to complementary overhangs between two consecutive gene fragments which are subsequently annealed and reamplified to generate a chimeric gene sequence (see, e.g., Current Protocols in Molecular Biology, eds. Ausubel et al. John Wiley & Sons, 1992). Moreover, many expression vectors are commercially available that already encode a fusion moiety (e.g., a GST polypeptide). A hnRNP L-encoding nucleic acid can be cloned into such an expression vector such that the fusion moiety is linked in-frame to the hnRNP L protein.

A recombinant expression vector contains a nucleic acid encoding hnRNP L in a form suitable for expression of the nucleic acid in a host cell, which means that the recombinant expression vector includes one or more regulatory sequences, selected on the basis of the host cells to be used for expression, which is operatively-linked to the nucleic acid to be expressed. Within a recombinant expression vector, operatively-linked is intended to mean that the nucleotide sequence of interest is linked to the regulatory sequence(s) in a manner which allows for expression of the nucleotide sequence (e.g., in an in vitro transcription/translation system or in a host cell). A regulatory sequence is intended to include promoters, enhancers and other expression control elements (e.g., polyadenylation signals). Such regulatory sequences are described, for example, in Goeddel (1990) Methods Enzymol. 185:3-7. Regulatory sequences include those which direct constitutive expression of a nucleic acid sequence in many types of host cells and those which direct expression of the nucleotide sequence only in certain host cells (e.g., tissue-specific regulatory sequences). It will be appreciated by one of skill in the art that the design of the expression vector depends on such factors as the choice of the host cell to be transformed, the level of expression of protein desired, and the like. The expression vector can be introduced into a host cell to thereby produce proteins or peptides of hnRNP L, isoforms of hnRNP L, mutant forms of hnRNP L, fusion proteins, and the like.

A recombinant expression vector can be designed for expression of hnRNP L protein in prokaryotic or eukaryotic cells. For example, hnRNP L proteins can be expressed in bacterial cells such as E. coli, insect cells (using baculovirus expression vectors), yeast cells or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve to increase expression of recombinant protein; increase the solubility of the recombinant protein; and aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion E. coli expression vectors include pTrc (Amann, et al., (1988) Gene 69:301-315) and pET 1d (Studier, et al. (1990) Methods Enzymol. 185:60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

A yeast expression vector is also contemplated. Examples of vectors for expression in yeast Saccharomyces cerevisiae include pYepSec 1 (Baldari, et al. (1987) EMBO J. 6:229-234), pMFa (Kurjan and Herskowitz (1982) Cell 30:933-943), pJRY88 (Schultz, et al. (1987) Gene 54:113-123), pYES2 (Invitrogen™ Corp., San Diego, Calif.), and picZ (Invitrogen™ Corp., San Diego, Calif.).

Alternatively, hnRNP L protein can be expressed in insect cells using baculovirus expression vectors. Baculovirus vectors available for expression of proteins in cultured insect cells (e.g., Sf9 cells) include the pAc series (Smith, et al. (1983) Mol. Cell. Biol. 3:2156-2165) and the pVL series (Lucklow and Summers (1989) Virology 170:31-39).

Further, nucleic acid molecules encoding hnRNP L are expressed in mammalian cells using a mammalian expression vector. As will be appreciated by one of skill in the art, hnRNP L expression in mammalian cells provides a means of purifying the proteins as well as a means of modulating the endogenous levels of hnRNP L protein in a cell. Examples of mammalian expression vectors include any one of the well-known recombinant viral vectors, pCDM8 (Seed (1987) Nature 329:840) and pMT2PC (Kaufman, et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, et al. Molecular Cloning: A Laboratory Manual. 2nd ed., Cold Spring Harbor Laboratory, Cold Spring Harbor Laboratory Press, Cold Spring Harbor, N.Y., 1989.

The recombinant mammalian expression vector may further be capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji, et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund, et al. (1985) Science 230:912-916), and mammary gland-specific promoters (e.g., milk whey promoter; U.S. Pat. No. 4,873,316 and EP 264,166). Developmentally-regulated promoters are also encompassed, for example the murine hox promoters (Kessel and Gruss (1990) Science 249:374-379) and the α-fetoprotein promoter (Campes and Tilghman (1989) Genes Dev. 3:537-546).

In addition to increasing the expression of hnRNP L to modulate the levels of hnRNP L present in the cell, hnRNP L expression can be decreased to modulate the levels of hnRNP L present in the cell. Thus, a recombinant expression vector harboring a nucleic acid encoding hnRNP L, or an iRNA target sequence thereof, cloned into the expression vector in an antisense orientation is also provided. That is, the nucleic acid encoding hnRNP L, or a target fragment thereof, is operatively-linked to a regulatory sequence in a manner which allows for expression (by transcription of the nucleic acid sequence) of an RNA molecule which is antisense to hnRNP L mRNA. Regulatory sequences operatively-linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type-specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, et al. (1986) Reviews-Trends in Genetics Vol. 1(1).

Host cells into which a hnRNP L nucleic acid can be introduced, e.g., a hnRNP L nucleic acid within a vector (e.g., a recombinant expression vector) or a hnRNP L nucleic acid containing sequences which allow it to homologously recombined into a specific site of the host cell's genome, are further contemplated. The terms host cell and recombinant host cell are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into prokaryotic or eukaryotic cells via conventional transformation or transfection techniques. As used herein, the terms transformation and transfection are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. supra and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the nucleic acid of interest. Preferred selectable markers include those which confer resistance to drugs, such as G418, hygromycin and methotrexate. Nucleic acids encoding a selectable marker can be introduced into a host cell on the same vector as that encoding an hnRNP L protein or can be introduced on a separate vector. Cells stably transfected with the introduced nucleic acid can be identified by drug selection (e.g., cells that have incorporated the selectable marker gene will survive, while the other cells die). A host cell, such as a prokaryotic or eukaryotic host cell in culture, can be used to produce (i.e., express) an hnRNP L protein.

The host cells can also be used to produce non-human transgenic animals. For example, a host cell is a fertilized oocyte or an embryonic stem cell into which hnRNP L-coding sequences have been introduced. Such host cells can then be used to create non-human transgenic animals in which exogenous hnRNP L sequences have been introduced into their genome or homologous recombinant animals in which endogenous hnRNP L sequences have been altered. Such animals are useful for studying the function and/or activity of an hnRNP L protein and for identifying and/or evaluating modulators of hnRNP L activity. As used herein, a transgenic animal is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a homologous recombinant animal is a non-human animal, preferably a mammal, more preferably a mouse, in which an endogenous hnRNP L gene has been altered by homologous recombination between the endogenous gene and an exogenous DNA molecule introduced into a cell of the animal, e.g., an embryonic cell of the animal, prior to development of the animal.

A transgenic animal can be created by introducing a hnRNP L-encoding nucleic acid into the male pronuclei of a fertilized oocyte, e.g., by microinjection or retroviral infection, and allowing the oocyte to develop in a pseudopregnant female foster animal. Alternatively, a non-human homologue of a human hnRNP L gene, such as a rat or mouse hnRNP L gene, can be used as a transgene. Intronic sequences and polyadenylation signals may also be included in the transgene to increase the efficiency of expression of the transgene. A tissue-specific regulatory sequence(s) can be operatively-linked to a hnRNP L transgene to direct expression of a hnRNP L protein to particular cells. Methods for generating transgenic animals via embryo manipulation and microinjection, particularly animals such as mice, have become conventional in the art and are described, for example, in U.S. Pat. Nos. 4,736,866; 4,870,009; 4,873,191; and in Hogan, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of an hnRNP L transgene in its genome and/or expression of hnRNP L mRNA in tissues or cells of the animals. A transgenic founder animal can then be used to breed additional animals carrying the transgene. Moreover, transgenic animals carrying a transgene encoding a hnRNP L protein can further be bred to other transgenic animals carrying other transgenes.

To create a homologous recombinant animal, a vector is prepared which contains at least a portion of an hnRNP L gene into which a deletion, addition or substitution has been introduced to thereby alter, e.g., functionally disrupt, the hnRNP L gene. The hnRNP L gene can be a human gene or a non-human homologue of a human hnRNP L gene. For example, a mouse hnRNP L gene can be used to construct a homologous recombination nucleic acid molecule, e.g., a vector, suitable for altering an endogenous hnRNP L gene in the mouse genome. The homologous recombination nucleic acid molecule may be designed such that, upon homologous recombination, the endogenous hnRNP L gene is functionally disrupted (i.e., no longer encodes a functional protein; also referred to as a knock out vector). Alternatively, the homologous recombination nucleic acid molecule can be designed such that, upon homologous recombination, the endogenous hnRNP L gene is mutated or otherwise altered but still encodes functional protein (e.g., the upstream regulatory region can be altered to thereby alter the expression of the endogenous hnRNP L protein). In the homologous recombination nucleic acid molecule, the altered portion of the hnRNP L gene is flanked at its 5' and 3' ends by additional nucleic acid sequence of the hnRNP L gene to allow for homologous recombination to occur between the exogenous hnRNP L gene carried by the homologous recombination nucleic acid molecule and an endogenous hnRNP L gene in a cell, e.g., an embryonic stem cell or fetal fibroblast. The additional flanking hnRNP L nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas and Capecchi (1987) Cell 51:503). The homologous recombination nucleic acid molecule is introduced into a cell, e.g., an embryonic stem cell line, by for example electroporation, and cells in which the introduced hnRNP L gene has homologously recombined with the endogenous hnRNP L gene are selected (see, e.g., Li, et al. (1992) Cell 69:915). The selected cells can then be injected into a blastocyst of an animal (e.g., a mouse) to form aggregation chimeras (see, e.g., Bradley, In: Teratocarcinomas and Embryonic Stem Cells: A Practical Approach, Robertson, E. J. ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are well-known (see, e.g., Bradley (1991) Current Opin. Biotechnol. 2:823-829; WO 90/11354; WO 91/01140; WO 92/0968; and WO 93/04169.

A method for identifying an agent that modulates the level or activity of hnRNP L is also encompassed by the instant invention. The method involves contacting a test cell containing hnRNP L protein, and a CA-dinucleotide rich sequence of the CD154 mRNA 3'-untranslated region operatively-linked to a nucleic acid encoding a reporter protein, with an agent and detecting reporter protein expression in the test cell. A decrease in reporter protein expression in the test cell contacted with the agent relative to reporter protein expression in a test cell not contacted with the agent, indicates that the agent increases the level or activity of hnRNP L in the cell. Conversely, an increase in reporter protein expression in the test cell contacted with the agent relative to reporter protein expression in a test cell not contacted with the agent, indicates that the agent decreases the level or activity of hnRNP L in the cell. Test cells expressing a reporter which can be used in accordance with the method of the invention are, in certain embodiments, mammalian cells including human cells.

The reporter gene sequence(s) can be inserted into a recombinant expression vector according to methods disclosed herein. More than one reporter gene can be inserted into the construct such that the test cells containing the resulting construct can be assayed by different means. The test cells which contain the nucleic acid encoding the reporter and which express the reporter can be identified by at least four general approaches; detecting DNA-DNA or DNA-RNA hybridization; observing the presence or absence of marker gene functions (e.g., resistance to antibiotics); assessing the level of transcription as measured by the expression of reporter mRNA transcripts in the host cell; and detecting the reporter gene product as measured by immunoassay or by its biological activity.

The test cells can be cultured under standard conditions of temperature, incubation time, optical density, plating density and media composition corresponding to the nutritional and physiological requirements of the cells. However, conditions for maintenance and growth of the test cell can be different from those for assaying candidate test compounds in the screening methods of the invention. Modified culture conditions and media are used to facilitate detection of the expression of a reporter molecule. Any techniques known in the art can be applied to establish the optimal conditions.

A reporter gene refers to any genetic sequence that is detectable and distinguishable from other genetic sequences present in test cells. Desirably, the reporter nucleic acid encodes a protein that is readily detectable either by its presence, or by its activity that results in the generation of a detectable signal. A nucleic acid encoding the reporter is used in the invention to monitor and report the translation of an RNA operatively-linked to a CA-dinucleotide rich sequence of a CD154 3'-untranslated region in test cells.

A variety of enzymes can be used as reporters including, but are not limited to, $\beta$-galactosidase (Nolan, et al. (1988) Proc. Natl. Acad. Sci. USA 85:2603-2607), chloramphenicol acetyltransferase (CAT; Gorman, et al. (1982) Molecular Cell Biology 2:1044; Prost, et al. (1986) Gene 45:107-111), $\beta$-lactamase, $\beta$-glucuronidase and alkaline phosphatase (Berger, et al. (1988) Gene 66:1-10; Cullen, et al. (1992) Methods Enzymol. 216:362-368). Transcription of the reporter gene leads to production of the enzyme in test cells. The amount of enzyme present can be measured via its enzymatic action on a substrate resulting in the formation of a detectable reaction product. The methods of the invention provide means for determining the amount of reaction product, wherein the amount of reaction product generated or the remaining amount of substrate is related to the amount of enzyme activity. For some enzymes, such as $\beta$-galactosidase, $\beta$-glucuronidase and $\beta$-lactamase, well-known fluorogenic substrates are available that allow the enzyme to covert such substrates into detectable fluorescent products.

A variety of bioluminescent, chemiluminescent and fluorescent proteins can also be used as light-emitting reporters in the invention. Exemplary light-emitting reporters, which are enzymes and require cofactor(s) to emit light, include, but are not limited to, the bacterial luciferase (luxAB gene product) of *Vibrio* harveyi (Karp (1989) Biochim. Biophys. Acta 1007: 84-90; Stewart, et al. (1992) J. Gen. Microbiol. 138:1289-1300), and the luciferase from firefly, *Photinus* pyralis (De Wet, et al. (1987) Mol. Cell. Biol. 7:725-737).

Other types of light-emitting reporter, which do not require substrates or cofactors, are wild-type green fluorescent protein (GFP) of Victoria aequoria (Chalfie, et al. (1994) Science 263:802-805), modified GFPs (Heim, et al. (1995) Nature 373:663-4; WO 96/23810), and the gene products encoded by the *Photorhabdus* luminescens lux operon (luxABCDE) (Francis, et al. (2000) Infect. Immun. 68(6):3594-600). Transcription and translation of these types of reporter genes leads to the accumulation of the fluorescent or bioluminescent proteins in test cells, which can be measured by a device, such as a fluorimeter, flow cytometer, or luminometer. Methods for performing assays on fluorescent materials are well-known in the art (e.g., Lackowicz, 1983, Principles of Fluorescence Spectroscopy, New York, Plenum Press).

For convenience and efficiency, enzymatic reporters and light-emitting reporters are desirable for the screening assays of the invention. Accordingly, the invention encompasses histochemical, colorimetric and fluorometric assays. An exemplary reporter construct, exemplified herein, contains the CA-dinucleotide rich sequence of a CD154 3'-untranslated region which regulates the translation of and therefore the expression of the reporter luciferase.

By way of illustration, a screening assay of the invention can be carried out by culturing a test cell containing a nucleic acid encoding luciferase operatively-linked to a CARE sequence of a CD154 3'-untranslated region; adding a test agent to a point of application, such as a well, in the plate and incubating the plate for a time sufficient to allow the test agent to effect luciferase mRNA translation; detecting luminescence of the test cells contacted with the test agent, wherein luminescence indicates expression of the luciferase polypeptide in the test cells; and comparing the luminescence of test cells not contacted with the test agent. A decrease in luminescence of the test cell contacting the test agent relative to the luminescence of test cells not contacting the test agent indicates that the test agent causes a decrease in the level or activity of hnRNP L. An increase in luminescence of the test cell contacting the test agent relative to the luminescence of test cells not contacting the test agent indicates that the test agent causes an increase in the level or activity of hnRNP L.

Agents which can be screened using the method provided herein encompass numerous chemical classes, though typically they are organic molecules, preferably small organic compounds having a molecular weight of more than 100 and less than about 2,500 daltons. Agents encompass functional groups necessary for structural interaction with proteins, particularly hydrogen bonding, and typically include at least an amine, carbonyl, hydroxyl or carboxyl group, preferably at least two of the functional chemical groups. The agents often contain cyclical carbon or heterocyclic structures and/or aromatic or polyaromatic structures substituted with one or more of the above functional groups. Agents can also be found among biomolecules including peptides, antibodies, saccharides, fatty acids, steroids, purines, pyrimidines, derivatives, structural analogs or combinations thereof. Agents are obtained from a wide variety of sources including libraries of natural or synthetic compounds.

A variety of other reagents such as salts and neutral proteins can be included in the screening assays. Also, reagents that otherwise improve the efficiency of the assay, such as protease inhibitors, nuclease inhibitors, anti-microbial agents, and the like can be used. The mixture of components can be added in any order that provides for the requisite binding.

Alternatively, antibodies against the hnRNP L can serve as the agent to inhibit (antagonize) or stimulate (agonize) hnRNP L activity. Whole hnRNP L or an epitope bearing fragment thereof can be used as an immunogen to produce antibodies immunospecific for hnRNP L. Various techniques well-known in the art can be used routinely to produce antibodies (Kohler and Milstein (1975) Nature 256:495-497; Kozbor, et al. (1983) Immunol. Today 4:72; Cole, et al. (1985) In: Monoclonal Antibodies and Cancer Therapy, pp 77-96).

Example 1 cDNA and siRNA Plasmids

The pcDNA 3.1/LUC and tetracycline responsive vector pTRE-LUC utilize the bovine growth hormone and beta globin polyadenylation signal sequences, respectively, and are known in the art (Hamilton, et al. (2003) Mol. Cell. Biol. 23:510-525). The murine CD154 3'-UTR corresponds to nucleotides (nt) 23-650 relative to the translational stop site was amplified from total cellular RNA from B6 splenocytes activated with PMA (10 ng/ml; Sigma, St. Louis, Mo.)+Ionomycin (IONO, 0.5 µM) and cloned into TOPO 2.1 (Invitrogen, Carlsbad, Calif.). Sequencing confirmed identity with GenBank Gene ID No. 560692. Deletion of the CURE (nt 127-228) or the CARE (nt 229-306) are referred to as CURE- and CARE-, respectively, while the CURE and CARE (nt 127-306) deletion is referred to as CU/CARE-. All were generated by QuikChange (Stratagene, La Jolla, Calif.) deletion from TOPO 2.1 as were the polycytidine and ARE mutations in the context of the CU/CARE- and confirmed by sequencing. These sequences were released by EcoRI and cloned into the XbaI site in pcDNA 3.1 firefly luciferase (pcDNA3.1/LUC) vector (Hamilton, et al. (2003) supra). For reporters containing only CURE (CURE+) and CARE (CARE+), the CURE or CARE was deleted from the CU/CARE- in TOPO 2.1 using QuikChange. The CURE and CARE were released from TOPO 2.1 and cloned into pcDNA 3.1 luciferase as described above. Generation of pTRE-Luc vectors containing the murine CD154 3'-UTR were released by EcoRI digestion from TOPO vectors described above and cloned into the EcoRV site downstream of the luciferase coding region. The CARE was cloned downstream of the polyadenylation signal sequence in the BamHI site of pGL3-promoter vector (Promega, Madison, Wis.).

SiRNA cDNA constructs targeting hnRNP L were purchased from Origene (Rockville, Md.); their activity was confirmed in HeLa cells by immunoblot analysis. Generation of pcDNA3.1-hnRNP L was achieved by the release of hnRNP L from pFASTBac hnRNP L through EcoRI and XhoI digestion and cloning into EcoRI and XhoI site in pcDNA 3.1

Example 2

Transient Transfection Assay of Reporter Gene Activity

Except for siRNA and hnRNP L overexpression studies, HeLa cells were transfected with 50 ng luciferase vectors, 1.5 µl lipofectamine (Invitrogen) and 4 µl PLUS (Invitrogen) in 0.5 ml RPMI for 3.5 hours at 37° C. 5% CO2, after which 0.5 mL RPMI+20% FCS was added. After 20 hours, cells were lysed and luciferase activity determined by luminometry. Individual experiments were analyzed for 3'-UTR-specific effects by dividing the mean luciferase activity from triplicate transfections of pcDNA3.1/LUC- or pTRE-LUC-based expression plasmids by that obtained from cells transfected with the corresponding control vector, which was assigned a value of 100%. In siRNA and hnRNP L overexpression experiments, cells were transiently transfected at day −2 with either 500 ng HuSH 303 or HuSH L79 or 250 ng empty pcDNA 3.1 control vector or pcDNA 3.1 hnRNP L followed by a repeat cotransfection of these plasmids along with the corresponding luciferase reporters at day 0, Separate cultures received equivalent amounts of the corresponding control (empty vector or containing an irrelevant RNA sequence) vector on day −2 and 0. Transient transfection of human PBMC was performed using AMAXA Nucleofection. After being transiently transfected overnight, luciferase activity was measured. Additional cultures were activated with PMA/IONO for 4 hours prior to analysis of luciferase activity.

Example 3

RNA Analysis by Quantitative RT-PCR

Cytoplasmic RNA was extracted according to known methods (Gough (1988) Anal. Biochem. 173:93-9). Nuclei were pelleted and resuspended in Solution 1 (10 mM Tris, 150 mM NaCl, 1.5 mM MgCl2 and 0.65% NP-40) and spun through a 30% sucrose cushion. Nuclear RNA was then extracted (Chomczynski & Sacchi (1987) Anal. Biochem. 162:156-159). Poly (A) RNA was purified using Oligotex beads (Qiagen, Valencia, Calif.). Subsequent qPCR analysis of input luciferase mRNA levels were measured using established methods (Hamilton, et al. (2003) supra). For studies of mRNA stability, Tet-Off HeLa cells (Clontech, Mountain View, Calif.) were purchased and carried according to manufacturer's instructions and transiently transfected as described above, allowed to recover overnight, then treated with Doxycycline (1 µg/ml) to shut off transcription for specified times. Analysis of the effects of priming on gene expression utilized cytoplasmic RNA that was digested with TurboDNase I (Ambion, Austin, Tex.) then reverse transcribed with either oligo d(T), random hexamers, or a luciferase-specific primer (5'-TTT GGC GGT TGT TAC TTG AC-3'; SEQ ID NO:2) and Superscript II RT (Invitrogen). Reverse transcription reactions were analyzed for luciferase transcripts using 5'-GGT GGC TCC CGC TGA ATT GG-3' (SEQ ID NO:3) and 5'-CCG TCA TCG TCT TTC CGT GC-3' (SEQ ID NO:4) primers. Oligo dT reverse transcriptions were analyzed for GAPDH transcripts RNA to control for input RNA (forward primer, 5'-acc acc ttc ttg atg tca tc-3' (SEQ ID NO:5) and reverse primer, 5'-CAA GGC TGT GGG CAA GGT CA-3' (SEQ ID NO:6)). Random Hexamer reverse transcriptions were analyzed for H4 histone RNA to control for input RNA (forward primer, 5'-CAA Cat tca ggg cat cac caa-3' (SEQ ID NO:7) and reverse primer 5'-CCC GAA TCA CAT TCT CCA AGA A-3' (SEQ ID NO:8)) and IQ SYBR Green Supermix (Bio-rad) by real-time PCR using a Bio-Rad iCycler. The luciferase/GAPDH or H4 transcript ratio was calculated for each sample, where Ct=threshold cycle and DCt=Luciferase Ct-GAPDH (dT primed reverse transcription) or H4 (Random Hexamer primed reverse transcription) Ct. DDCt=DCt1-DCt2, where DCt1 is CD154 and DCt2 is control. Fold Difference=2-DDCt.

In these experiments, the percent inhibition of CD154 3'-UTR-dependent luciferase expression seen with each vector and priming method was calculated and then divided by the inhibition seen with the empty control vector, which was assigned a value of 100%. In some instances, data was presented where the DCt obtained with oligo (dT) priming for a given transfection was subtracted from that obtained with random hexamer priming (DCtRH.-DCtdT).

Example 4

Immunoprecipitation Analysis

HeLa cells were transiently transfected as specified and cultured overnight or human PBMC were activated for 24 hours with PMA 10 ng/ml and IONO 1 µM. Cytoplasmic and nuclear extracts were obtained using conventional methods (Rigby, et al. (1999) J. Immunol. 163:4199-206), with the addition of Protector RNase (Roche, Indianapolis, Ind.). Extracts were immunoprecipitated in parallel with 4D11 (anti-RNP L) and BB7 (anti-PTB) antibodies as well as a mouse IgG isotype control bound to protein-A Sepharose beads (Pharmacia, Piscataway, N.J.). Beads were washed six times in 150 mM NaCl, boiled in SDS-PAGE loading buffer and resolved by 12% SDS-PAGE and immunoblotted. Remaining beads were digested with proteinase K (Roche), then extracted with phenol-chloroform. Following DNase I digestion, the presence of human CD154 or luciferase mRNA in each precipitation was measured by oligo d(T)-based reverse transcription and qPCR. Human CD154 primers included 5'-TTG CGG GCA ACA ATC CAT TCA CTT-3' (SEQ ID NO:9) and 5'-GTG GGC TTA ACC GCT GTG CTG TAT T-3' (SEQ ID NO:10).

Example 5

Analysis of Poly(A) Tail Length

For native CD154 mRNA polyadenylation assay, murine T cells were purified from a B6 spleen or volunteer donor by negative selection using the EasySep® Mouse T Cell Enrichment Kit (StemCell Technologies), and subsequently activated with CD3/CD28 (Dynal). Poly (A) tail length was measured by LM-PAT assay (Salles, et al. (1999) supra), in which the 3' end of the poly (A) tail was hybridized to a primer containing oligo (dT)16 5'-GCG AGC TCC GCG GCC GCG (T)16-3' (SEQ ID NO:11) containing a GC 'anchor' sequence (Operon). Target mRNA (100 ng) was incubated and with phosphorylated oligo(dT)16 (Roche) at an unfavorable annealing temperature (42° C.) in the presence of T4 DNA ligase (Invitrogen) saturating the poly (A) tail, thereby creating an oligo (dT) copy of the poly A tail. At 42° C., the 3' end of the poly (A) tail remains largely unpaired due to unfavorable hybridization conditions. The oligo (dT)-GC anchor sequence was added at 10-fold molar excess and the temperature reduced to 12° C., enabling selective hybridization to the unpaired 3' ends. Reverse transcription was performed (Superscript II Reverse Transcriptase, Invitrogen) followed by PCR using a primer corresponding to the GC-rich sequence in the oligo-(dT) anchor along with a primer specific for the mRNA to be analyzed. Primers used for LM-PAT assay included: Luciferase, 5'-GCC ATC TGT TGT TTG CC-3' (SEQ ID NO:12); mCD154, 5'-CTG TCT ACA GCA CTG TCG GG-3' (SEQ ID NO:13); mTNF, 5'-CAC CTG GCC TCT CTA CCT TG-3' (SEQ ID NO:14). Primers were designed so that the PCR product encoded a restriction enzyme sites MnlI, AseI and HphI, respectively. Products were resolved by agarose gel electrophoresis and the identity of the visualized band confirmed by restriction enzyme digestion.

What is claimed is:

1. A method for inhibiting the nuclear export or translation of a ribonucleic acid comprising: contacting an isolated cell or tissue containing a CA-dinucleotide rich sequence of the CD154 mRNA 3'-untranslated region operatively-linked to a heterologous ribonucleic acid with an agent which binds to the CA-dinucleotide rich sequence, wherein said agent is selected from the group consisting of a purified hnRNP L protein, and a recombinant expression vector expressing hnRNP L protein, and a recombinant expression vector expressing an siRNA which binds the CA-dinucleotide rich sequence or hnRNP L, so that the nuclear export or translation of the ribonucleic acid is inhibited.

* * * * *

```
SEQUENCE LISTING

<160> NUMBER OF SEQ ID NOS: 14

<210> SEQ ID NO 1
<211> LENGTH: 365
<212> TYPE: DNA
<213> ORGANISM: Homo sapiens

<400> SEQUENCE: 1
caggctctag aacgtctaac acagtggaga accgaaaccc cccccccccc cccgccacc      60 ctctcggaca gttattcatt ctctttcaat ctctctctct ccatctctct ctttcagtct    120
ctctctctca acctctttct tccaatctct ctttctcaat ctctctgttt ccctttgtca    180
gtctcttccc tcccccagtc tctcttctct cccccttttct aacacacaca cacacacaca    240
```

```
cacacacaca cacacacaca cacacacaca cacacacaca cacacagagt caggccgttg    300
ctagtcagtt ctcttctttc caccctgtcc ctatctctac cactatagat gagggtgagg    360
agtag                                                                365

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
tttggcggtt gttacttgac                                                 20

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
ggtggctccc gctgaattgg                                                 20

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
ccgtcatcgt ctttccgtgc                                                 20

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
accaccttct tgatgtcatc                                                 20

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
caaggctgtg ggcaaggtca                                                 20

<210> SEQ ID NO 7
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 7
caacattcag ggcatcacca a                                               21

<210> SEQ ID NO 8
```

<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 8
cccgaatcac attctccaag aa                                              22

<210> SEQ ID NO 9
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 9
ttgcgggcaa caatccattc actt                                            24

<210> SEQ ID NO 10
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 10
gtgggcttaa ccgctgtgct gtatt                                           25

<210> SEQ ID NO 11
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 11
gcgagctccg cggccgcgtt tttttttttt tttt                                 34

<210> SEQ ID NO 12
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 12
gccatctgtt gtttgcc                                                    17

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
ctgtctacag cactgtcggg                                                 20

<210> SEQ ID NO 14
<211> LENGTH: 18
<212> TYPE: DNA
<213> ORGANISM: Artificial sequence
<220> FEATURE:
<223> OTHER INFORMATION: Synthetic oligonucleotide

```
<400> SEQUENCE: 14
cacctggcct ctctacct                                                    18
```